(12) United States Patent
Lee et al.

(10) Patent No.: US 9,128,033 B2
(45) Date of Patent: Sep. 8, 2015

(54) MULTIPLE SURFACE ACOUSTIC WAVE SENSOR SYSTEM

(75) Inventors: Hun Joo Lee, Hwaseong-si (KR); Soo Suk Lee, Suwon-si (KR); Yeul ho Lee, Seoul (KR); Youn Suk Choi, Gyeonggi-do (KR)

(73) Assignee: SAMSUNG ELECTRONICS CO., LTD., Suwon-Si (KR)

(*) Notice: Subject to any disclaimer, the term of this patent is extended or adjusted under 35 U.S.C. 154(b) by 481 days.

(21) Appl. No.: 13/296,372

(22) Filed: Nov. 15, 2011

(65) Prior Publication Data

US 2012/0058546 A1    Mar. 8, 2012

Related U.S. Application Data

(63) Continuation-in-part of application No. 12/775,004, filed on May 6, 2010.

(30) Foreign Application Priority Data

Nov. 6, 2009    (KR) .................. 10-2009-0106934

(51) Int. Cl.
   *G01N 27/00*    (2006.01)
   *G01N 29/24*    (2006.01)
   *G01N 29/02*    (2006.01)
   *G01N 33/543*   (2006.01)

(52) U.S. Cl.
   CPC .......... *G01N 29/2462* (2013.01); *G01N 29/022* (2013.01); *G01N 33/54373* (2013.01); *G01N 2291/02466* (2013.01)

(58) Field of Classification Search
   CPC ............ G01N 29/2462; G01N 29/024; G01N 2291/0427
   USPC .......... 422/68.1; 310/313 B, 313 R, 318, 319
   See application file for complete search history.

(56) References Cited

U.S. PATENT DOCUMENTS

| | | |
|---|---|---|
| 4,932,255 A | 6/1990 | Brace et al. |
| 5,235,235 A | 8/1993 | Martin et al. |
| 5,488,866 A | 2/1996 | Ravel et al. |
| 5,763,283 A | 6/1998 | Cernosek et al. |
| 6,321,588 B1 | 11/2001 | Bowers et al. |
| 2002/0032531 A1 | 3/2002 | Mansky et al. |
| 2003/0201694 A1* | 10/2003 | Lu et al. .................... 310/313 A |
| 2006/0034726 A1* | 2/2006 | Sunshine et al. ............. 422/58 |
| 2008/0230859 A1* | 9/2008 | Zaghloul et al. ............. 257/428 |

\* cited by examiner

Primary Examiner — Natalia Levkovich
(74) Attorney, Agent, or Firm — Leydig, Voit & Mayer, Ltd.

(57) ABSTRACT

Provided is a multiple SAW sensor system capable of sensing a plurality of target materials in the SAW sensor with a single detector by using a multiplexer. According to the multiple SAW sensor system, the target materials in SAW sensors may be sensed with a single detector, thereby avoiding unnecessary power loss. Also, a plurality of target materials in a sample may be sensed, thereby reducing a waste of the sample.

16 Claims, 8 Drawing Sheets

Conventional SAW sensor system

MULTIPLE SURFACE ACOUSTIC WAVE SENSOR SYSTEM

CROSS-REFERENCE TO RELATED APPLICATION

This is a continuation-in-part of application Ser. No. 12/775,004 filed May 6, 2010.

BACKGROUND

1) Field

The disclosure relates to a multiple surface acoustic wave ("SAW") sensor system, more particularly, to a multiple SAW sensor system capable of sensing a plurality of target materials in the SAW sensor with a single detector by using a multiplexer.

2) Description of the Related Art

A Surface Acoustic Wave ("SAW") sensor is an element or a device for detecting or measuring an absolute value of a physical quantity or a chemical quantity, a change in physical quantity or chemical quantity, or intensity of a sound, light, or a radio wave from a target using a base and surface sensing technique and a SAW, and for converting them into an electrical signal.

Generally, the SAW sensor is disposed on a substrate made of a piezoelectric material, and includes a receptor that binds to a target material on a surface of the SAW sensor. Thus, when a sample containing the target material flows to the SAW sensor, a wavelength is changed due to a physical, chemical or electrical reaction between the target material and the receptor. The resulting change is used to determine or monitor the content of the target material.

For a biosensor, when a biomolecule, such as a protein, antibody, antigen, deoxyribonucleic acid ("DNA"), ribonucleic acid ("RNA"), bacteria, an animal cell, a virus or tissue, and a toxin generated therefrom, binds to a surface of the biosensor, a surface mass of the sensor changes, and thereby a signal drift occurs in the sensor. As a result, the biosensor can determine or monitor the content of the target material.

Methods for monitoring the change of a wavelength in the SAW sensor are generally divided into two types. A first type is an oscillation method of checking the change of the wavelength in the SAW sensor by re-applying an output signal emitted from the SAW sensor to the SAW sensor as an input signal. A second type of method for monitoring the change of the wavelength in the SAW sensor is measuring the change of the wavelength by applying a specific frequency, generated outside the SAW sensor, to an input inter-digital transducer ("IDT") electrode of the SAW sensor and plotting output signals according to frequencies.

SUMMARY

Provided is a multiple SAW sensor system capable of sensing a plurality of target materials in the SAW sensor with a single detector by using a multiplexer.

According to an aspect, a multiple SAW sensor system comprising: SAW sensors; a first multiplexer connected to input parts of the SAW sensors; a second multiplexer connected to output parts of the SAW sensors; an oscillator connected between the first multiplexer and the second multiplexer; a channel controller including a first port connected to the first multiplexer, and a second port connected to the second multiplexer, which applies a channel selection signal to at least one of the first multiplexer and the second multiplexer; and a detector connected to the oscillator, which senses an electrical signal from the second multiplexer, is disclosed.

The SAW sensor may include a piezoelectric substrate; an input part on one side of the piezoelectric substrate, which converts the electrical signal into the SAW; a sensing part on the piezoelectric substrate, which outputs a SAW corresponding to the target materials so as to sense the target materials when the SAW is input from the input part; and an output part on one side of the piezoelectric substrate, which converts the corresponding SAW into the electrical signal.

According to another aspect, a multiple SAW sensor system comprising: SAW sensors; a signal generator connected to input parts of the SAW sensors; a multiplexer connected to output parts of the SAW sensors, which selects one of electrical signals from the output parts of the SAW sensors; and a detector which senses the electrical signal from the multiplexer, is disclosed.

According to the multiple SAW sensor system, the target materials in SAW sensors may be sensed with a single detector, thereby avoiding unnecessary power loss. Also, a plurality of target materials in a sample may be sensed, thereby reducing a waste of the sample.

BRIEF DESCRIPTION OF THE DRAWINGS

The above and other aspects of the invention will become more readily apparent by describing in further detail example embodiments thereof with reference to the accompanying drawings, in which.

DETAILED DESCRIPTION

Figure 1:
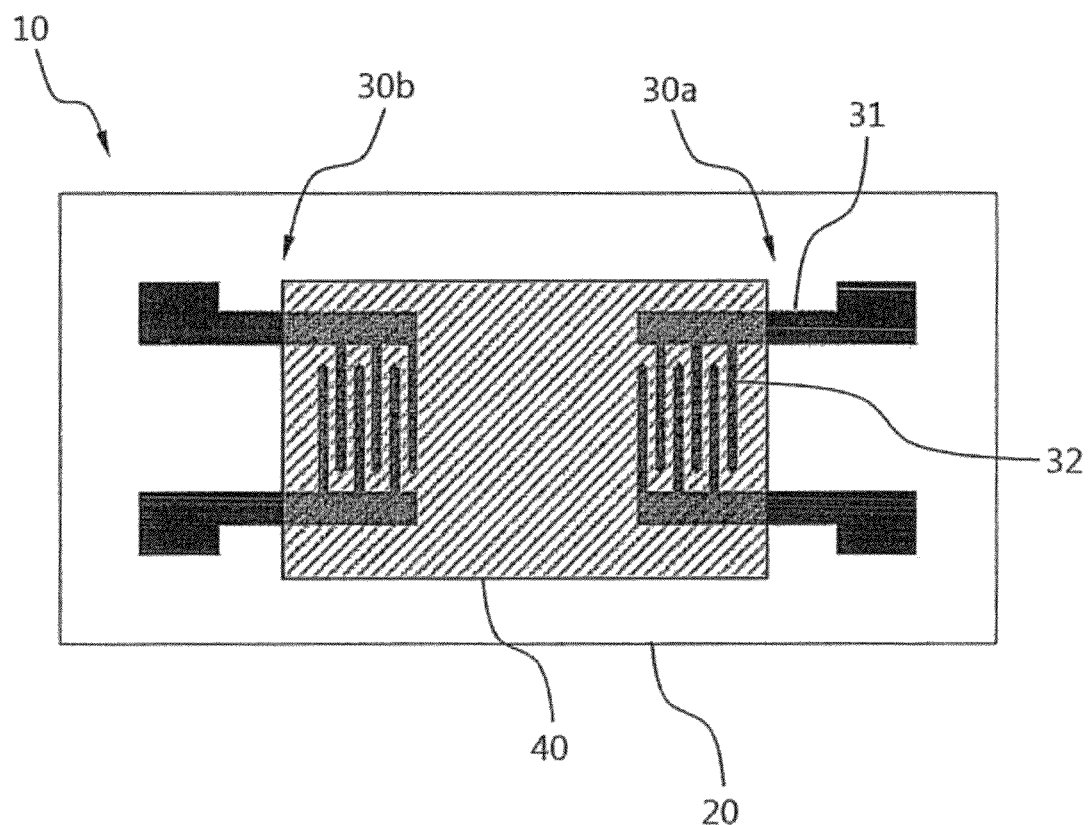
FIG. 1 is a plan view of a unit surface acoustic wave ("SAW") sensor of a multiple SAW sensor system.

The invention now will be described more fully hereinafter with reference to the accompanying drawings, in which a non-limiting embodiment is shown. This invention may, however, be embodied in many different forms, and should not be construed as limited to the example embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the disclosure, and will not be interpreted in an idealized or overly formal sense unless expressly so defined herein.

One or more embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear portions. Moreover, sharp angles that are illustrated may be rounded. Thus, the regions illustrated in the figures are schematic in nature and their shapes are not intended to illustrate the precise shape of a region and are not intended to limit the scope of the claims.

Hereinafter, embodiments of the invention will be described in further detail with reference to the accompanying drawings.

Surface Acoustic Wave

As used herein, the term "surface acoustic wave ("SAW")" refers to a mechanical wave motion rather than an electromagnetic wave, which is generated from movement of particles due to various causes such as external thermal, mechanical, or electrical forces. As the SAW typically includes vibration energy concentrated on a surface of an elastic body, it is propagated along the surface of a solid as an earthquake is propagated along the ground.

A wave propagated through a medium is typically divided into a longitudinal wave, a transversal wave and a surface wave. The longitudinal wave occurs when a particle displacement sends waves in substantially the same direction as that of an original wave, the transversal wave occurs when a particle displacement sends waves perpendicular to that of the original wave, and the surface wave occurs by a vector sum of the longitudinal wave and the transversal wave.

Generally, about 90 percent (%) or more of a longitudinal displacement component and a transversal displacement component vanishes within a length of one wavelength of a material surface, and most energy thereof is concentrated within the length of one wavelength inside the surface. Thus, the SAW is also called a transversal wave or a Rayleigh wave.

SAWs are typically classified into shear horizontal SAWs ("SH SAWs") and surface transverse waves ("STWs") according to types and classified into flexural plate waves ("FPWs"), Love waves, surface skimming bulk waves, and Lamb waves according to a purpose of use, but is not limited thereto. Among these, the Lamb wave is mainly used for sensing a gas, and the Love wave is mainly used for sensing a liquid.

SAW Sensor System

Provided is a multiple SAW sensor system capable of sensing a plurality of target materials in the SAW sensor with a single detector by using a multiplexer. According to the multiple SAW sensor system, the target materials in SAW sensors may be sensed with a single detector, thereby avoiding unnecessary power loss. Also, a plurality of target materials in a sample may be sensed, thereby reducing a waste of the sample.

As used herein, the term "target material" refers to a subject material to be sensed, e.g., a molecule to be recognized by a sensing part in a SAW sensor.

As used herein, the term "sample" refers to any material capable of containing a target material. The biological sample may be, but is not limited to, blood or any component thereof (for example, plasma or serum), menstrual fluid, mucus, sweat, tears, urine, feces, saliva, sputum, semen, cerebrospinal fluid, genital secretions, gastric lavage fluid, pericardial or abdominal fluid or lavage fluid, a throat swab, pleural lavage fluid, ear wax, hair, skin cells, nails, mucosae, aqua amnii, leukorrhea or any bodily liquid, spinal fluid, a gaseous sample containing breath or body smell of a human, flatulence or other gas, any biological tissue or material, or an extract or suspension thereof.

As used herein, the term "SAW sensor" refers to a device for sensing presence and absence or a physical property or a chemical property of the target material using the SAW.

The SAW sensor may convert an electrical signal into a SAW, and sense the target material using the SAW, and then convert a SAW output corresponding to the target into an electrical signal. The SAW sensor may include a piezoelectric substrate, an input part, a sensing part, and an output part. A plan view of a SAW sensor is shown in FIG. 1.

As used herein, the term "piezoelectric substrate 20" refers to a substrate including a piezoelectric material.

The piezoelectric material has an electrical characteristic that is changed when a mechanical signal is applied (i.e., piezoelectric effect). Conversely, a mechanical signal is generated when an electrical signal is applied (i.e., the reverse piezoelectric effect). The piezoelectric material may include a metallic oxide or an insulating material. For example, the material of the piezoelectric substrate may include, but is not limited to, lithium niobate ("LiNbO$_3$"), lithium tantalite ("LiTaO$_3$"), lithium tetraborate ("Li$_2$B$_4$O$_7$"), barium titanate ("BaTiO$_3$"), lead zirconate ("PbZrO$_3$"), lead titanate ("PbTiO$_3$"), lead zirconate titanate ("PZT"), zinc oxide ("ZnO"), gallium arsenide ("GaAs"), quartz or niobate.

As used herein, the term "input part 30$b$" refers to an area which converts an electrical signal applied from the signal generator into a SAW, which is a mechanical signal.

The input part 30$b$ may include an interdigital transducer ("IDT"). The input part 30$b$ may further include an electrode pad for receiving an electrical signal from the signal generator which is formed on one end of the input part 30$b$.

The input part 30$b$ may be formed by patterning a metallic material onto the piezoelectric substrate 20 into a previously set form. The metallic material may include a thin film metal such as an aluminum alloy, a copper alloy, or gold, for example, but is not limited thereto. In order to prevent corrosion of the metallic material due to exposure to atmosphere or moisture, a protective layer such as an anti-oxidation layer may be disposed on a surface of the metallic material.

As used herein, the term "sensing part 40" is disposed on the piezoelectric substrate 20, and refers to an area capable of outputting the SAW corresponding to the target so as to sense the target when the SAW is input from the input part 30$b$. The sensing part may be configured by a delay line between the input part 30$b$ and the output part 30$a$, and may include a film form or a cell form.

When the target is contacted to the surface of the sensing part, due to influence of various types of causes such as pressure, rotator force, shock, tensile force, gravity, mass, evaporation, biochemistry, temperature, humidity, freezing, viscosity, displacement, liquidity, light sensing, optic angle, acceleration, abrasion, contamination, a SAW that is substantially different in frequency, phase, amplitude, or the number of clocks from that of a SAW sent from the input part may be generated.

The target material may include protein, DNA, viruses, bacteria, cell, tissue, gas, temperature, humidity, but is not limited thereto.

As used herein, the term "output part 30$a$" is disposed on one side of the piezoelectric substrate 20, and refers to an area capable of converting a mechanical signal into an electrical signal so as to analyze the SAW which is output and received from the sensing part. The output part 30$a$ may be formed at an opposite side to the input part 200 with the sensing part interposed therebetween.

The output part 30$a$ may be in the form similar to that of the input part 30$b$ or modified from the input part 30$b$. The output part 30$a$ may include an electrode pad for outputting a signal to the signal measuring part on one end of the output part.

The output part 30$a$ may be formed by patterning a metallic material onto the piezoelectric substrate 20 into a previously set form. The metallic material is substantially the same as in the input part 200.

As used herein, the term "multiplexer" refers to any device capable of functioning as a multiplexer, a demultiplexer, or both the multiplexer and the demultiplexer. The multiplexer ("MUX") is a device that selects one of several input signals and forwards the selected input signal into a single line. The demultiplexer ("DeMUX") is a device taking a single input signal and selecting one of many data-output-lines, which is connected to the single input.

According to an embodiment, a multiple SAW sensor system using an oscillation method is provided. The multiple SAW sensor system may include SAW sensors; a first multiplexer connected to input parts of the SAW sensors; a second multiplexer connected to output parts of the SAW sensors; an oscillator connected between the first multiplexer and the second multiplexer; a channel controller including a first port connected to the first multiplexer, and a second port connected to the second multiplexer, which applies a channel selection signal to at least one of the first multiplexer and the second multiplexer; and a detector connected to the oscillator, which senses an electrical signal from the second multiplexer.

Figure 2:
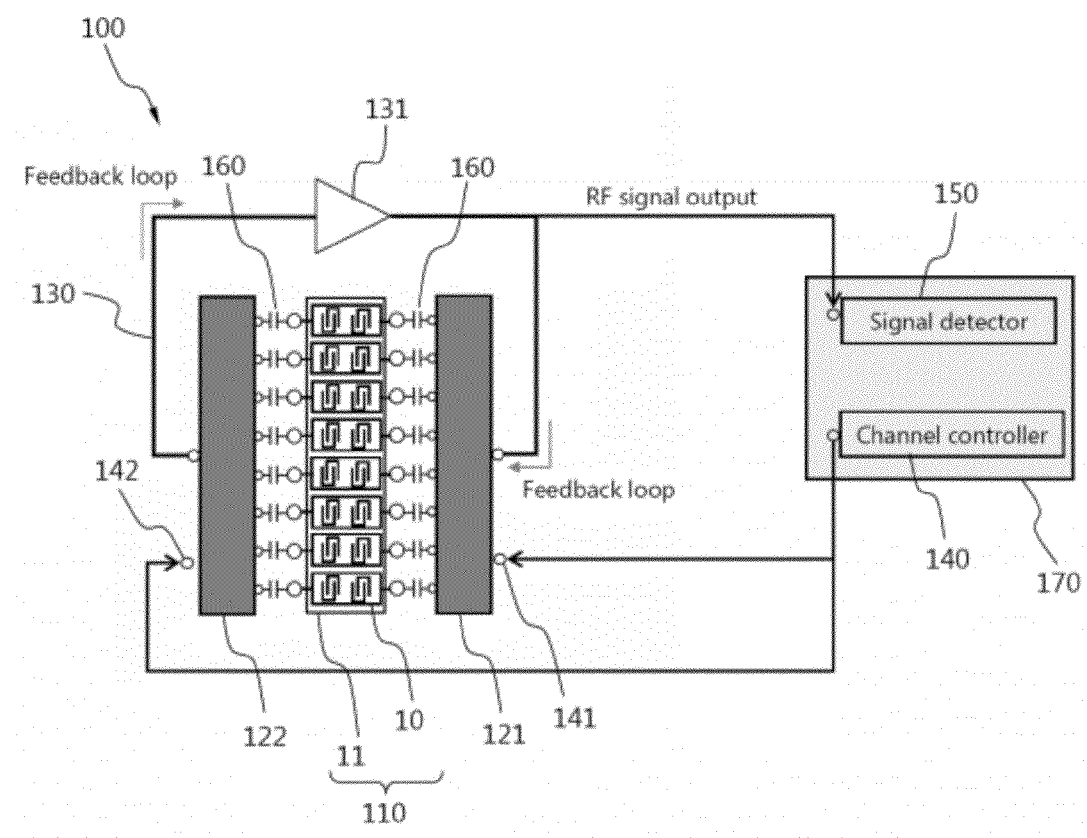
FIG. 2 is a schematic circuit diagram of an embodiment of a multiple SAW sensor system.

An exemplary embodiment of the multiple SAW sensor system is shown in FIG. 2.

Referring to FIG. 2, the SAW sensor system 100 includes a SAW sensor array 110 including a plurality of unit SAW sensors 10. For example, eight of the unit SAW sensors 10 shown in FIG. 1 may constitute the SAW sensor array 110 of FIG. 2, but alternative exemplary embodiments are not limited thereto.

The SAW sensor system 100 includes a first multiplexer 121 and a second multiplexer 122. The first multiplexer 121 and the second multiplexer 122 are connected to input parts and output parts, respectively, of the SAW sensor array 110. The first multiplexer 121 is connected to an input parts of the SAW sensor array 110, and the second multiplexer 122 is connected to an output parts of the SAW sensor array 110.

The SAW sensor system 100 may further include an oscillator 130 connected between the first multiplexer 121 and the second multiplexer 122, and formed with a feedback loop circuit. The oscillator 130 transmits an electrical oscillation signal to the SAW sensor array 110 through the first multiplexer 121, and transmits an electrical signal generated from the SAW sensor array 110 and transmitted through the second multiplexer 122 to the first multiplexer 121.

The oscillator 130 may further include an amplifier 131 for amplifying an electrical signal transmitted through the second multiplexer 122. The oscillator 130 may further include an attenuator (not shown) connected between the second multiplexer 122 and the amplifier 131, and a low-pass filter (not shown) connected between the amplifier 131 and the first multiplexer 121.

The SAW sensor system 100 may further include a channel controller 140 and a detector 150. The channel controller 140 and the detector 150 may be implemented in one integrated circuit ("IC") 170. The channel controller 140 is connected to the first multiplexer 121 through a first port 141, and is connected to the second multiplexer 122 through a second port 142, and thus applies the same channel selection signal to the first multiplexer 121 and the second multiplexer 122 through the first port 141 and the second port 142, respectively. Therefore, a desired one of the SAW sensors of the SAW sensor array 110 may be selected.

Since the detector 150 is connected to the oscillator 130, the detector 150 detects signals which has been generated from the SAW sensors and transmitted through the second multiplexer 122. When channels are sequentially altered by providing signals to the first multiplexer 121 and the second multiplexer 122, the channel controller 140 determines an address of a signal value output from the SAW sensor, and stores the signal of each channel without changing signals between the SAW sensors. In one or more example embodiments, the detector 150 and the channel controller 140 may be configured in separate chips, not in one integrated circuit 170.

The SAW sensor system 100 may further include a plurality of capacitors 160. The capacitors 160 may be disposed between the input part of the SAW sensor array 110 and the first multiplexer 121, as well as between the output part of the SAW sensor array 110 and the second multiplexer 122.

The multiple SAW sensor system may sense a plurality of target materials in the SAW sensor arrays including the plurality of SAW sensors at one time with a single detector by using the multiplexer.

An example embodiment of a method for sensing a target material from a sample using the multiple SAW sensor system will now be described in further detail.

For example, when N target materials are contained in the sample, an array including N SAW sensors binding to receptors capable of binding to respective target materials is formed.

To observe a reaction of a target material with a first SAW sensor, channel selection signals from the channel controller to the first SAW sensor are inputted to the first multiplexer and the second multiplexer.

The reference frequency is inputted to an input part of the first SAW sensor through the first multiplexer, and if the target material binds to the receptor, the frequency is altered, and thus an altered frequency is outputted from an output part of the first SAW sensor. The output frequency is transmitted to the oscillator through the second multiplexer.

Accordingly, the output frequency is sensed using the detector, and compared with the reference frequency to sense the frequency change. The reference frequency may be a frequency that corresponds to a condition in which the target material is not present in the sample.

The channel selection signals are altered in the channel controller, and the procedure described above is repeated, thereby detecting the presence of the N target materials in the one sample.

According to another embodiment, a multiple SAW sensor system using a phase method is provided. The multiple SAW sensor may comprises SAW sensors; a signal generator connected to input parts of the SAW sensors; a multiplexer connected to output parts of the SAW sensors, which selects one of electrical signals from the output parts of the SAW sensors; and a detector, which senses an electrical signal from the multiplexer. An exemplary embodiment of the multiple SAW sensor system is shown in FIG. 3.

Figure 3:
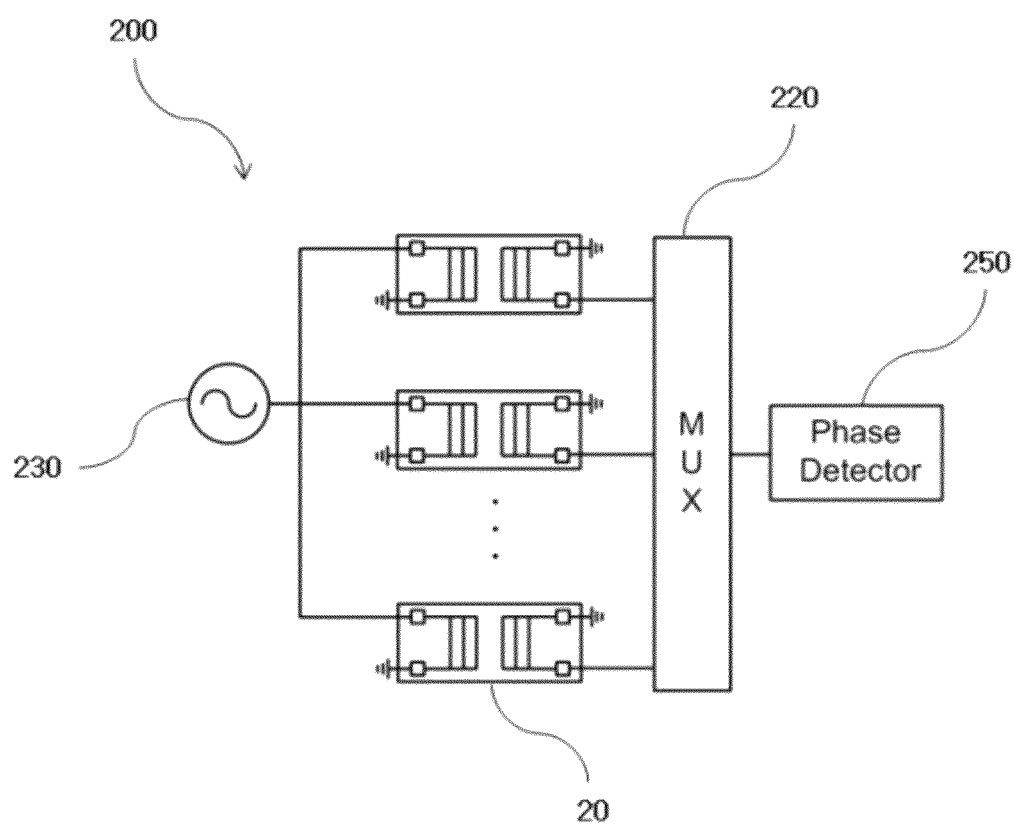
FIG. 3 is a schematic circuit diagram of another embodiment of a multiple SAW sensor system.

Referring to FIG. 3, the SAW sensor system 200 includes a SAW sensor array including a plurality of unit SAW sensors. For example, at least two SAW sensors 20 shown in FIG. 1 may constitute the SAW sensor array of FIG. 3, but alternative exemplary embodiments are not limited thereto.

The SAW sensor system 200 includes a signal generator 230. Alternatively, in this position, an oscillator may be placed. The signal generator 230 may be connected to an input part of the SAW sensor array, or be connected to a multiplexer where the multiplexer is connected to the input part of the SAW sensor array. The signal generator 230 transmits a desired electrical signal to the SAW sensor array.

The SAW sensor system 200 includes a multiplexer 220 which selects one of the output signals. The multiplexer may be connected to the output part of the SAW sensor array, or connected to the input part and output part of the SAW sensor array The SAW sensor system 200 may further include a plurality of capacitors (not shown). The capacitors may be connected between the input part of the SAW sensor array and the multiplexer, or be connected between the output part of the SAW sensor array and the multiplexer.

The SAW sensor system 200 may further include a detector 250. The detector is connected to the multiplexer 220, and measures a change in frequency or phase of the electrical signal which is generated from a plurality of the SAW sensor and is transmitted through the multiplexer. The detector may include an apparatus such as a frequency counter, a network analyzer, a vector voltmeter or an oscilloscope, but is not limited thereto.

An example embodiment of a method for sensing a target material from a sample using the multiple SAW sensor system will now be described in further detail.

For example, when N target materials are contained in the sample, an array including N SAW sensors binding to receptors capable of binding to respective target materials is formed.

First, an electrical signal generated by a signal generator is inputted to input parts of the SAW sensor.

If the target materials respectively bind to the receptors of the SAW sensor, the phase is altered, and thus an altered phase is outputted from an output part of the SAW sensor.

Then, a desired electrical signal from the outputted electrical signal is selected by the multiplexer, the change in phase of the selected electrical signal is measured by the detector, such as a network analyzer. Therefore, by the reaction of the target material in the sample with the receptor, the change in mass, pressure, density and viscosity may be detected.

Presence and absence of the target material in the respective SAW sensor is sensed by changing the selection of the electrical signal outputted from the SAW sensor using the multiplexer.

Hereinafter, the embodiment will be described in further detail with reference to specific examples, which are compared each other. It will be noted that these examples described herein are merely provided to illustrate different example embodiments, but the scope of the present invention is not limited to the examples described and shown herein.

For Example 1, and as shown in FIG. 2, a SAW sensor system is configured such that an array including eight integrated SAW unit sensor 10 (A1 through A8) is connected to a first and second multiplexers, and one oscillator is formed through one feedback loop circuit connected to the first and second multiplexers.

Figure 4:
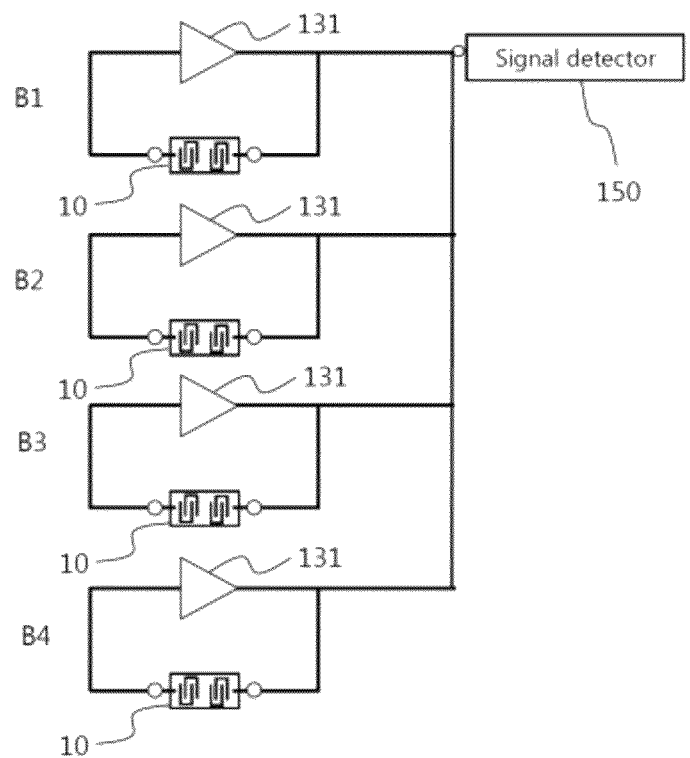
FIG. 4 is a schematic circuit diagram of a conventional SAW sensor system.

For comparative Example 1, and as shown in FIG. 4, which is a schematic circuit diagram of a conventional SAW sensor system, separate feedback loop circuits corresponding to four SAW unit sensors 10 (B1 through B4) are formed, thereby configuring a SAW sensor system having four oscillators.

Figure 5:
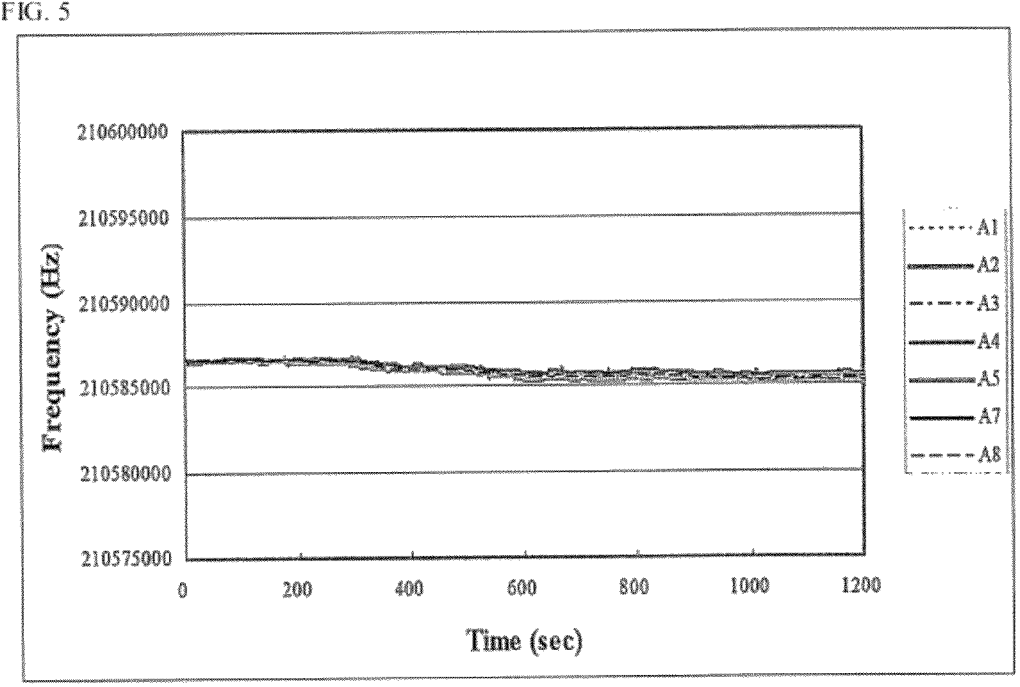
FIG. 5 is a graph of frequency versus time showing frequency stabilities of experimental example of an embodiment of SAW sensors.
Figure 6:
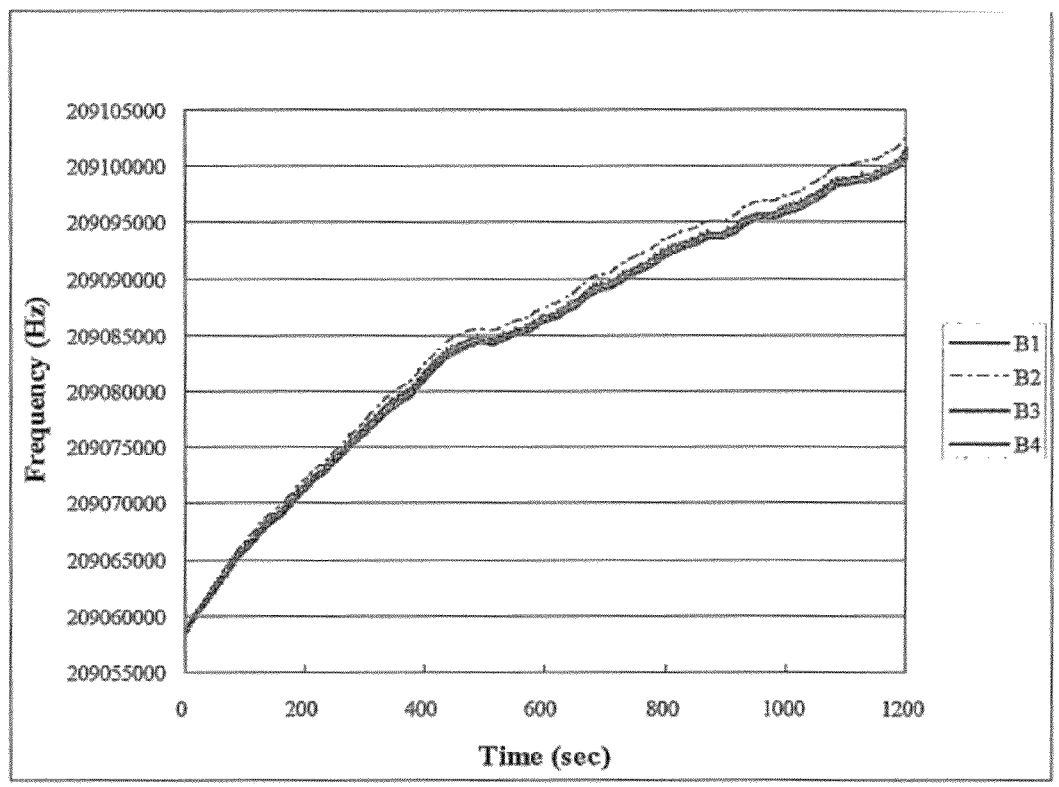
FIG. 6 is a graph of frequency versus time showing frequency stabilities of comparative example of an embodiment of SAW sensors.

For Experimental Example 1, a phosphate buffer saline ("PBS") solution flowed to the SAW sensor systems in Example 1 and Comparative Example 1 in a no-stress state, and signal drifts are measured to check frequency stability. The results are shown in FIGS. 5 and 6, which are graphs of frequency, in Hertz (Hz), versus time, in seconds (sec), showing frequency stabilities of comparative and experimental example embodiments of SAW sensors.

For Example 1, each of the eight SAW unit sensors (A1 through A8) is measured every two seconds, and one cycle was 16 seconds. For Comparative Example 1, the four SAW unit sensors (B1 through B4) are used to measure the frequency stability. As deviation between the SAW signals decreases, the frequency stability is improved. Thus, as can be seen from Table 1 below and FIG. 5, the results are much better than for a comparative Example 1, conventional SAW sensor system.

TABLE 1

| | Average Standard Deviation ("stDEV") | |
|---|---|---|
| | Example 1 | Comparative Example 1 |
| 5 minutes | 134.4 | 563.59 |
| 10 minutes | 162.6 | 668.431 |
| 20 minutes | 339.4 | 954.096 |

Figure 7:
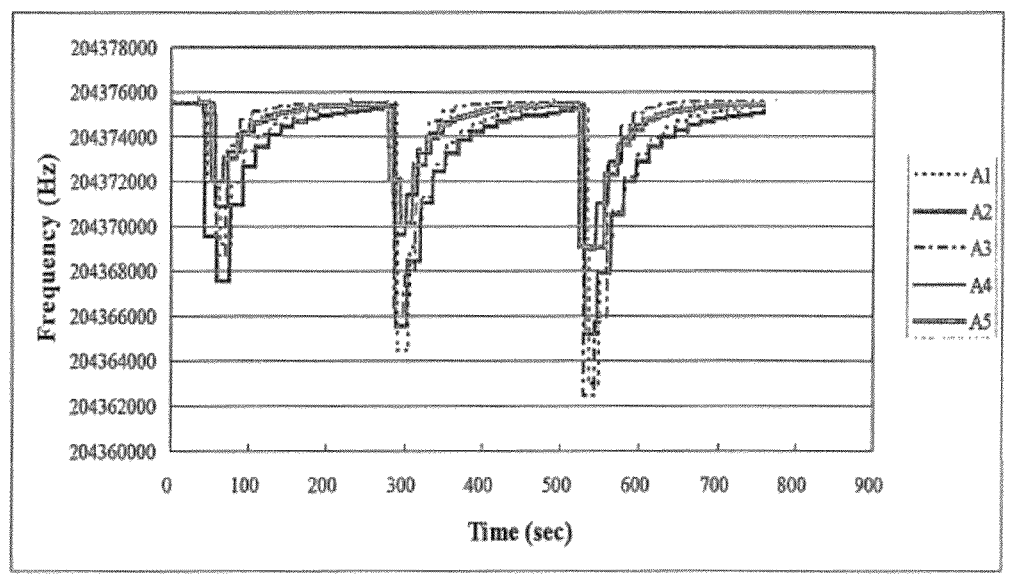
FIG. 7 is a graph of frequency versus time showing frequency changes of experimental example of an embodiment of SAW sensors.
Figure 8:
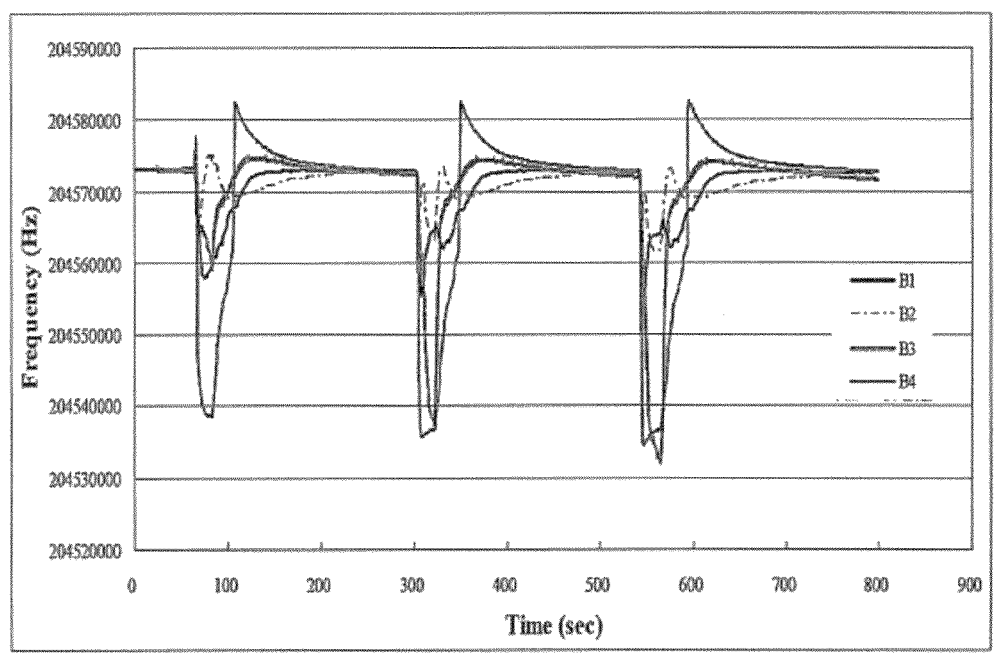
FIG. 8 is a graph of frequency versus time showing frequency changes of comparative example of an embodiment of SAW sensors.

For Experimental Example 2, in the SAW sensor systems in Example 1 (A1 through A5) and Comparative Example 1 (B1 through B4), samples flows of 500, 1000, and 1500 microliters per minute (μl/min) on the PBS solution are provided, and degrees of recovering frequencies changed by a pressure gradient to a normal state are measured. The results of the frequency change caused by a pressure gradient and the recovery to the normal frequency are shown in FIGS. 7 and 8, which are graphs of frequency (in Hz) versus time (in sec) showing frequency stabilities of comparative and experimental example embodiments of SAW sensors. In addition, average standard deviations are calculated, and are shown in Table 2, below.

Referring to Table 2 and FIG. 7, as the deviation between the SAW signals decreases, a recovery deviation is smaller. Thus, as shown in Table 2 and FIG. 6, it can be seen that the result of Example 1 is much better than that of Comparative Example 1.

TABLE 2

| | Average Standard Deviation (stDEV) | |
|---|---|---|
| Flow Rate | Example 1 | Comparative Example 1 |
| 500 μl/minute | 94.8 | 148.4 |
| 1000 μl/minute | 91.9 | 239.2 |
| 1500 μl/minute | 182.1 | 262.0 |

The invention should not be construed as being limited to the example embodiments set forth herein. Rather, these example embodiments are provided so that this disclosure will be thorough and complete and will fully convey the concept of the present invention to those of ordinary skill in the art.

In addition, while the invention has been particularly shown and described with reference to example embodiments thereof, it will be understood by those of ordinary skill in the art that various changes in form and details may be made therein without departing from the spirit or scope of the present invention as defined by the following claims.

What is claimed is:

1. A multiple surface acoustic wave sensor system, the system comprising:
a controller;
surface acoustic wave sensors;
a signal generator connected to input parts of the surface acoustic wave sensors;
a first multiplexer connected to input parts of the surface acoustic wave sensors, wherein the first multiplexer selects one of the surface acoustic wave sensors;
a second multiplexer connected to output parts of the surface acoustic wave sensors, wherein the second multiplexer selects an output electrical signal; and
a detector configured to detect the selected output electrical signal;
wherein the controller is communicatively coupled to the first multiplexer and the second multiplexer and configured to control the first multiplexer and the second multiplexer.

2. The system of claim 1, wherein each of the surface acoustic wave sensors comprises:
a piezoelectric substrate;
an input part disposed on the piezoelectric substrate, wherein the input part converts an input electrical signal from the signal generator into a surface acoustic wave;
a sensing part disposed on the piezoelectric substrate configured to contact a target material; and
an output part disposed on the piezoelectric substrate, wherein the output part converts the surface acoustic wave into an output electrical signal.

3. The system of claim 2, wherein the sensing part is configured to contact a target material comprising at least one selected from the group consisting of protein, DNA("Deoxyribonucleic acid"), viruses, bacteria, cell, tissue, gas, and moisture.

4. The system of claim 1, further comprising capacitors connected between the input parts of the surface acoustic wave sensors and the first multiplexer, and between the output parts of the surface acoustic wave sensors and the second multiplexer.

5. The system of claim 1, wherein the detector is configured to detect a change in frequency or phase of the electrical signal.

6. The system of claim 1, wherein the detector comprises a frequency counter, a network analyzer, a vector voltmeter, or an oscilloscope.

7. The system of claim 1, wherein the signal generator is configured to generate a surface acoustic wave comprising a flexural plate wave, a Love wave, a surface skimming bulk wave, or a Lamb wave.

8. The system of claim 2, wherein the input part and the output part are interdigital transducers.

9. The system of claim 1, further comprising a channel controller connected to a first port of the first multiplexer and a second port of the second multiplexer, wherein the channel controller outputs a channel selection signal to the first port and the second port.

10. The system of claim 9, wherein the channel controller and the detector are disposed on a common integrated circuit.

11. The system of claim 1, further comprising:
a feedback loop connecting the first multiplexer to the second multiplexer; and
an amplifier disposed in the feedback loop, wherein the amplifier amplifies at least one electrical signal output from the second multiplexer.

12. The system of claim 11, wherein the signal generator comprises an oscillator, and the oscillator is part of the feedback loop.

13. The system of claim 12, further comprising:
an attenuator in the feedback loop; and
a low-pass filter in the feedback loop.

14. The system of claim 13, wherein:
the oscillator is connected between the second multiplexer and the attenuator;
the attenuator is connected between the oscillator and the amplifier;
the amplifier is connected between the attenuator and the low-pass filter;
the low-pass filter is connected between the amplifier and the first multiplexer.

15. The system of claim 12, wherein the surface acoustic wave sensors each comprise:

a piezoelectric substrate;

an input part disposed on the piezoelectric substrate, the input part converts an input electrical signal into an input surface acoustic wave;

a sensing part disposed on the piezoelectric substrate and configured to contact a target material; and an output part disposed on the piezoelectric substrate, the output part converts the modified surface acoustic wave into an output electrical signal.

16. A multiple surface acoustic wave sensor system, the system comprising:

surface acoustic wave sensors;

a signal generator connected to input parts of the surface acoustic wave sensors;

a first multiplexer connected to input parts of the surface acoustic wave sensors, wherein the first multiplexer selects one of the surface acoustic wave sensors;

a second multiplexer connected to output parts of the surface acoustic wave sensors, wherein the second multiplexer selects an output electrical signal;

a detector configured to detect the selected output electrical signal; and capacitors connected between the input parts of the surface acoustic wave sensors and the first multiplexer, and between the output parts of the surface acoustic wave sensors and the second multiplexer.

* * * * *